United States Patent [19]
Ushio et al.

[11] Patent Number: 5,962,340
[45] Date of Patent: *Oct. 5, 1999

[54] HOMOGENEOUS IMMUNOASSAY METHOD UTILIZING 5-300 MM MAGNESIUM

[75] Inventors: Yoshihiro Ushio; Futoshi Kanke, both of Amagasaki, Japan

[73] Assignee: Wako Pure Chemical Industries Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/540,972

[22] Filed: Oct. 11, 1995

[30] Foreign Application Priority Data

Nov. 2, 1994 [JP] Japan ................................. 6-293718

[51] Int. Cl.$^6$ ................................................ G01N 33/539
[52] U.S. Cl. .......................... 436/539; 436/533; 436/546; 435/7.94
[58] Field of Search ................... 436/539, 533, 436/546; 435/7.94

[56] References Cited

U.S. PATENT DOCUMENTS

| | | | |
|---|---|---|---|
| 4,132,767 | 1/1979 | Tohmatsu et al. | 424/1 |
| 4,134,792 | 1/1979 | Boguslaski | 195/99 |
| 4,169,012 | 9/1979 | Dawson et al. | 435/7 |
| 4,234,564 | 11/1980 | McAleer | 424/12 |
| 4,298,592 | 11/1981 | Lin | 424/1 |
| 4,302,536 | 11/1981 | Longnecker | 435/7 |
| 4,481,291 | 11/1984 | Gils | 435/6 |
| 4,579,825 | 4/1986 | Siedel et al. | 436/175 |
| 4,708,939 | 11/1987 | Siedel et al. | 436/13 |
| 4,740,458 | 4/1988 | Kondo et al. | 435/15 |
| 4,746,605 | 5/1988 | Kerscher et al. | 437/7 |
| 4,843,021 | 6/1989 | Noguchi et al. | 436/533 |
| 4,902,630 | 2/1990 | Bennett et al. | 436/546 |
| 4,920,045 | 4/1990 | Okuda et al. | 435/7 |
| 5,055,395 | 10/1991 | Toth | 435/7.33 |
| 5,281,522 | 1/1994 | Senyei et al. | 435/7.9 |
| 5,358,852 | 10/1994 | Wu | 435/7.94 |
| 5,378,620 | 1/1995 | Adams | 435/183 |
| 5,441,869 | 8/1995 | Dressauer | 435/7.1 |
| 5,633,166 | 5/1997 | Westgard et al. | 436/8 |
| 5,728,589 | 3/1998 | Ushio | 436/543 |
| 5,773,304 | 6/1998 | Hino et al. | 436/174 |

FOREIGN PATENT DOCUMENTS

| | | |
|---|---|---|
| 2008060 | 7/1990 | Canada . |
| A-0 379 133 | 7/1990 | European Pat. Off. . |
| WO A-94 24558 | 10/1994 | WIPO . |

OTHER PUBLICATIONS

Journal: Association of Official Analytical Chemists; vol. 66, No. 1, Jan. 1983; pp. 184–187; T. Chiang et al.
Database WPI, week 8611; Derwent Pub. Ltd., AN 86–073589 & JP-A-61 025 062 (Nissui Seiyaku KK), Feb. 3, 1986; Abstract.
Database WPI, week 9323; Derwent Pub. Ltd., AN 93–185518 & JP-A-05 113 442 (Sinotest KK), May 7, 1993; Abstract.
Freise, J. et al, J. Clin. Chem. Clin. Biochem., vol. 15(9), 1977, p 485–488.
Funke, H. et al., Clin. Chem. 1982, vol. 28(5), p 1153–1158.
Heuck, C. et al., Clin. Chem. vol. 29(1) p 120–125, 1983.
Assmann, G et al, 1983, Clin. Chem. vol. 29(12), p 2026–2030.
Schriewien, H. et al, J. Clin. Chem. Clin. Biochem, vol. 23, 1985, p. 355–359.
Riepponen, P. et al, Scan. J. Clin. Lab. Inves. 1987, vol. 47, p 739–44.
Grafmeyer, D. et al, Eur. J. Clin. Chem. Clin. Biochem., 1995, vol. 33, p 31–52.
Heuck et al, 1983, Clin. Chem., vol. 29(1), p 120–125.
Schriewer et al (1985), J. Clin. Chem. Clin. Biochem. vol. 23, pp. 355–359.

*Primary Examiner*—James C. Housel
*Assistant Examiner*—Ginny Allen Portner
*Attorney, Agent, or Firm*—Armstrong, Westerman Hattori, McLeland & Naughton

[57] ABSTRACT

In a method for immunoassay of a trace component in a sample derived from a living body on the basis of a change of turbidity or scattered light intensity caused by antigen-antibody reaction, when the antigen-antibody reaction is carried out in the presence of magnesium ions previously added, an analyte can be measured rapidly and easily with high precision and reproducibility.

12 Claims, No Drawings

HOMOGENEOUS IMMUNOASSAY METHOD UTILIZING 5-300 MM MAGNESIUM

BACKGROUND OF THE INVENTION

This invention relates to an immunoassay method in which for example, when a component in a body fluid such as serum, plasma, etc. is measured, only this objective substance can be quantitated rapidly with high precision by suppressing or avoiding the influence of a nonspecific turbidity produced by a combination of a component other than the substance to be measured in a test sample and a component in a reagent solution on the measurement.

In recent years, autoanalyzers capable of analyzing many samples for many items at the same time have spread, and attempts have been made to apply to the autoanalyzers a method for measuring a trace component in a sample derived from a living body, on the principle of so-called immunoturbidimetry (TIA) in which an objective component is measured by measuring a turbidity change caused by antigen-antibody reaction, or so-called immunonephelometry (NIA) in which an objective component is measured by measuring a scattered light intensity change caused by antigen-antibody reaction.

Such methods, however, are disadvantageous in that high-precision measurement of an analyte to be measured is hindered by a turbidity (chyle) due to a lipoprotein present in a sample or a so-called non-specific turbidity, i.e., a turbidity produced by the reaction of a component in a reagent solution with, for example, a complement (e.g. Clq), rheumatoid factor (RF) or a heat-denatured protein produced by decomplementation by heating.

For avoiding the influence of chyle on the measurement, a method comprising previous addition of a surfactant to a reagent solution is known. However, the nonspecific turbidity due to, for example, Clq, RF or the heat-denatured protein is very difficult to avoid even by use of a surfactant. In practice, no surfactant effective for such a purpose has been found and put to practical use. Therefore, for assay of trace components in samples derived from living bodies, there is desired the development of a method which permits suppression or avoidance of measurement errors caused by insoluble materials produced by the reaction of a reagent solution with, for instance, Clq, RF or the heat-denatured protein in the sample.

SUMMARY OF THE INVENTION

The present invention was made in view of such conditions and is intended to provide a method and a reagent which make it possible, in assay of trace components in samples derived from living bodies, to measure an analyte to be measured, rapidly and easily with high precision and reproducibility by suppressing or reducing the nonspecific turbidity due to, for example, Clq, RF or the heat-denatured protein in the sample.

The present invention provides an immunoassay method for determining the concentration of a component in a living body fluid, which comprises
  subjecting a sample from a living body fluid and a reaction reagent to an antigen-antibody reaction in the presence of magnesium ions previously added, and
  measuring a change in turbidity or a change in scattering light intensity caused by the antigen-antibody reaction.
The present invention also provides a reagent for immunoassay, which comprises an antibody or antigen to a component in a sample to be measured and magnesium ions.

DESCRIPTION OF THE PREFERRED EMBODIMENTS

In order to find a method for measuring an analyte to be measured, with high precision by suppressing or avoiding measurement errors caused by the nonspecific turbidity due to, for instance, Clq, RF or the heat-denatured protein in immunoturbidimetry and immunonephelometry, the present inventors earnestly investigated and consequently found that this purpose can be achieved by carrying out an antigen-antibody reaction in the presence of magnesium ions previously added, whereby the present invention has been accomplished.

The measuring method of the present invention is practiced by employing measuring conditions (e.g. reaction time, measuring wavelength, etc.) and a measuring procedure which are employed in a conventional immunoturbidimetry or immunonephelometry method utilizing antigen-antibody reaction, except that the antigen-antibody reaction should be carried out in the presence of magnesium ions previously added. For the measurement by the method of the present invention, there can be used without exception all of other reagents, autoanalyzers, spectrophotometers and the like which are usually used in the art.

According to the present invention, the antigen-antibody reaction between a sample from a living body fluid and a reaction reagent is carried out in the presence of magnesium ions previously added.

The words "previously added" mean that magnesium ions are made to be present in a reaction solution before the antigen-antibody reaction or at the beginning of the antigen-antibody reaction. In order to make such a state, various methods are possible. For example, a solution (e.g. a buffer solution) containing magnesium ions is prepared first, followed by mixing with a sample from a living body fluid containing a component to be measured (i.e. analyte), and a reaction reagent containing an antigen or antibody to the analyte to give a reaction solution. Another method is to add magnesium ions to a sample from a living body fluid (i.e. analyte), followed by mixing with a reaction reagent containing an antigen or antibody to the analyte to give a reaction solution. A further method is to add magnesium ions to a reaction reagent containing an antigen or antibody to the analyte, followed by mixing with a sample from a living body fluid (i.e. analyte) to give a reaction solution.

Although the concentration of the magnesium ions used in the present invention is varied depending on the amount of a sample, the concentration in the reaction solution in which the antigen-antibody reaction is carried out is properly chosen in the range of usually 5 to 300 mM, preferably 30 to 300 mM, more preferably 50 to 300 mM. Magnesium ions may originally be present in a living body fluid, but the concentration is about 1 mM at most, which value is insufficient to carry out the present invention. Thus, the magnesium ions are previously added so as to make the concentration in the above-mentioned ranges. When the magnesium ion concentration is too much, the antigen-antibody reaction is depressed (inhibited), so that the desired measurement cannot be carried out with high precision. Therefore, care should be taken.

In the present invention, as the source of magnesium ions, there can be used various salts. Although the kind of the salt used in this case is not particularly limited so long as the salt neither deteriorates the stability of reagents present in the solution nor inhibits the antigen-antibody reaction, preferable examples of the salt are salts with inorganic acids such as sulfuric acid, nitric acid, etc., salts (halides) with halogen atoms such as chlorine, bromine, iodine, etc., and salts with organic acids such as acetic acid, gluconic acid, propionic acid, pantothenic acid, etc.

As the reaction reagent, there can be used the following ones; when the analyte is an antigen, the corresponding antibody is used, while when the analyte is an antibody, the corresponding antigen is used. Needless to say, the reaction reagent may further contain a buffer solution, a reaction accelerator, an antiseptic, a stabilizer, and other additives conventionally used in this art.

As a buffer solution usable in the measuring method of the present invention, there can be exemplified all of those usually used in immunoturbidimetry or immunonephelometry, such as Tris buffers, phosphate buffers, veronal buffers, borate buffers, Good's buffers, etc. The pH at the reaction for measurement is not particularly limited so long as it does not inhibit the antigen-antibody reaction. Usually, the pH is preferably chosen in the range of 6 to 10.

A reaction accelerator (an agglutination accelerator) [e.g. a polyethylene glycol, polyvinyl alcohol, dextran, etc.] may be present in the reaction solution used in the present invention, in a concentration range usually employed in the art. Needless to say, even under such conditions, the non-specific turbidity due to, for instance, Clq, RF or the heat-denatured protein can be suppressed or reduced.

As the living body fluid, there can be used serum, plasma, urine, lymph, cerebrospinal fluid, etc.

The analyte to be measured which is measurable by the measuring method of the present invention is not particularly limited and any analyte may be used so long as it is usually measurable by immunoturbidimetry or immunonephelometry. Preferable examples of the analyte are C-reactive protein (CRP), immunoglobulin G (IgG), immunoglobulin A (IgA), immunoglobulin M (IgM), ASO (Antistreptolysin O), albumin, urinary trace albumin, complement C3, complement C4, transferrin, haptoglobin, α-fetoprotein (AFP), etc.

In the immunoassay method of the present invention, a change in turbidity (immunoturbidimetry) or a change in scattering light intensity (immunonephelometry) caused by the antigen-antibody reaction is measured by a conventional method. The immunoturbidimetry is disclosed, for example, in "Rinsho Kensa-ho Teiyo, 30ed, 2th print, p 851–853 (1993), published by Kanehara Shuppan Co., Ltd. The immunonephelometry is disclosed, for example, on p 853–854 of the same publication as mentioned above.

The immunoturbidimetry and immunonephelometry can be carried out using a conventionally used analyzing device such as an autoanalyzer, a spectrophotometer, etc.

The reagent for immunoassay of the present invention comprises an antibody or antigen to a component in a sample to be measured and magnesium ions. The reagent for immunoassay may further contain one or more additives such reaction accelerators, buffers, antiseptics, stabilizers in effective amounts conventionally used. Examples of the stabilizers are saccharides, proteins, surfactants, etc.

The present invention is more concretely described with reference to the following examples, which are not by way of limitation but by way of illustration.

EXAMPLE 1

Screening of various metal ions (1) Samples for Measurement

Sera each having a predetermined RF value were prepared as samples for measurement by using Interference Check RF (a trade name, International Reagent Co., Ltd.; freeze-dried product) and human serum (RF: less than 30 IU/ml). The RF values were measured by use of RF-HA Test Wako (mfd. by Wako Pure Chemical Industries, Ltd.) according to the standard procedure described in the operating manual.

(2) Samples for Obtaining a Calibration Curve

Physiological saline (150 mM NaCl; CRP concentration: 0 mg/dl) and CRP standard (available from Wako Pure Chemical Industries, Ltd.; CRP nominal value: 6.2 mg/dl) were used as samples for obtaining a calibration curve.

(3) Reagent Solutions for Reaction

① Buffer Solutions (First Reagent Solutions)

As first reagent solutions, there were used 50 mM 3-(N-morpholino)propanesulfonic acid (MOPS)-NaOH buffer solutions (pH 7.4) containing 3.0 w/v % polyethylene glycol 6,000, 0.1 w/v % $NaN_3$ and a predetermined concentration of a predetermined metal salt.

② Anti-CRP Solution (Second Reagent Solution)

As a second reagent solution, there was used a 50 mM MOPS-NaOH buffer solution (pH 7.4) containing 2.0 mg Ab/ml anti-human CRP rabbit serum (available from Wako Pure Chemical Industries, Ltd.), 150 mM NaCl and 0.1 w/v % $NaN_3$.

(4) CRP Value Measurement by Immunoturbidimetry

Measuring Procedure

The measurement was carried out as follows by means of an Autoanalyzer Hitachi Model 7070.

After 10 μl of each predetermined sample for measurement and 250 μl of each first reagent solution were mixed and then incubated at 37° C. for 5 minutes, absorbance (referred to as "absorbance A") at a wavelength of 340 nm was measured. Subsequently, 50 μl of the anti-CRP solution (second reagent solution) was poured into the reaction solution and the reaction was carried out at 37° C. for 5 minutes, followed by measurement of absorbance (referred to as "absorbance B") at a wavelength of 340 nm. The absorbance change caused by the reaction was calculated from the obtained absorbances A and B according to the following equation:

$$\text{Absorbance change} = (\text{absorbance B}) - (260/310) \times (\text{absorbance A})$$

The same measuring procedure as above was carried out using the same reagent solutions as described above, except that the each sample for obtaining a calibration curve was used in place of the sample for measurement. The absorbance changes at CRP concentrations of 0 and 6.2 mg/dl, respectively, were calculated, and on the basis of the calculated values, a calibration curve showing the relationship between absorbance change and CRP concentration was obtained. Using the calibration curve, the CRP concentration of each sample for measurement was calculated from the absorbance change calculated for the sample for measurement.

Results

The results obtained are shown in Table 1.

reagent solution, the sodium chloride concentration and the magnesium chloride concentration were adjusted so that the

TABLE 1

Screening of Various Metal Ions

| Salt concentration | Sodium chloride | | Potassium chloride | | Lithium chloride | | Sodium fluoride | | Sodium bromide | | Sodium nitrate | |
|---|---|---|---|---|---|---|---|---|---|---|---|---|
| in reaction solution RF in sample for measurement (IU/ml) | 120 mM CRP value (mg/dl) | 240 mM CRP value (mg/dl) | 120 mM CRP value (mg/dl) | 240 mM CRP value (mg/dl) | 120 mM CRP value (mg/dl) | 240 mM CRP value (mg/dl) | 120 mM CRP value (mg/dl) | 240 mM CRP value (mg/dl) | 120 mM CRP value (mg/dl) | 240 mM CRP value (mg/dl) | 120 mM CRP value (mg/dl) | 240 mM CRP value (mg/dl) |
| 30 ↓ | 0.24 | 0.25 | 0.22 | 0.22 | 0.26 | 0.32 | −0.96 | −0.59 | 0.24 | 0.25 | 0.25 | 0.25 |
| 205 | 0.96 | 0.95 | 0.82 | 0.75 | 0.81 | 0.86 | −0.10 | −0.18 | 0.81 | 0.69 | 0.40 | 0.35 |
| 410 | 1.80 | 1.81 | 1.74 | 1.51 | 1.77 | 1.58 | −0.52 | −0.30 | 1.83 | 1.40 | 1.57 | 1.40 |

| Salt concentration | Sodium nitrite | | sodium sulfate | | Calcium chloride | | Magnesium chloride | | Strontium chloride | | Calcium acetate | |
|---|---|---|---|---|---|---|---|---|---|---|---|---|
| in reaction solution RF in sample for measurement (IU/ml) | 120 mM CRP value (mg/dl) | 240 mM CRP value (mg/dl) | 120 mM CRP value (mg/dl) | 240 mM CRP value (mg/dl) | 120 mM CRP value (mg/dl) | 240 mM CRP value (mg/dl) | 120 mM CRP value (mg/dl) | 240 mM CRP value (mg/dl) | 120 mM CRP value (mg/dl) | 240 mM CRP value (mg/dl) | 120 mM CRP value (mg/dl) | 240 mM CRP value (mg/dl) |
| 30 ↓ | −0.30 | −0.08 | 0.35 | 0.29 | 0.26 | 0.24 | 0.25 | 0.25 | 0.28 | 0.23 | 0.31 | 0.23 |
| 205 | −0.20 | −0.11 | 0.87 | 0.74 | 1.33 | 1.43 | 0.41 | 0.40 | 0.71 | 0.66 | 0.84 | 0.71 |
| 410 | 1.00 | −0.26 | 1.71 | 1.52 | 1.83 | 2.54 | 0.52 | 0.53 | 1.13 | 1.02 | 1.71 | 1.48 |

| Salt concentration | Magnesium acetate | | Strontium acetate | | Calcium sulfate | | Magnesium sulfate | |
|---|---|---|---|---|---|---|---|---|
| in reaction solution RF in sample for measurement (IU/ml) | 120 mM CRP value (mg/dl) | 240 mM CRP value (mg/dl) | 120 mM CRP value (mg/dl) | 240 mM CRP value (mg/dl) | 120 mM CRP value (mg/dl) | 240 mM CRP value (mg/dl) | 120 mM CRP value (mg/dl) | 240 mM CRP value (mg/dl) |
| 30 ↓ | 0.24 | 0.25 | 0.27 | 0.29 | 0.27 | | 0.23 | 0.24 |
| 205 | 0.43 | 0.42 | 0.89 | 0.73 | 0.80 | | 0.39 | 0.40 |
| 410 | 0.51 | 0.51 | 1.66 | 1.47 | 1.80 | | 0.53 | 0.52 |

From the results shown in Table 1, it can be seen that measurement errors due to RF can be markedly reduced by the presence of magnesium ions. In addition, the results shown in Table 1 indicate that this effect of magnesium ions is independent of the kind of anions (chloride ions, sulfate ions, acetate ions, etc.).

EXAMPLE 2

Investigation on magnesium ion concentration (1) Samples for Measurement

Sera each having a predetermined RF value were prepared as samples for measurement by using Interference Check RF (a trade name, International Reagent Co., Ltd.; freeze-dried product) and human serum (RF: less than 18 IU/ml). The RF values were measured by use of RF-HA Test Wako (mfd. by Wako Pure Chemical Industries, Ltd.) according to the standard procedure described in the operating manual.

(2) Samples for Obtaining a Calibration Curve

Physiological saline (150 mM NaCl; CRP concentration: 0 mg/dl) and CRP Standard (available from Wako Pure Chemical Industries, Ltd.; CRP nominal value: 6.2 mg/dl) were used as samples for obtaining a calibration curve.

(3) Reagent Solutions for Reaction

① Buffer Solutions (First Reagent Solutions)

As first reagent solutions, there were used 50 mM MOPS-NaOH buffer solutions (pH 7.4) containing 3.0 w/v % polyethylene glycol 6,000, 0.1 w/v % $NaN_3$ and a predetermined concentration of sodium chloride and a predetermined concentration of magnesium chloride. In each first reagent solution, the sodium chloride concentration and the magnesium chloride concentration were adjusted so that the total concentration (concentration at reaction) of these salts in a final reaction solution might be 300 mM.

② Anti-CRP Solution (Second Reagent Solution)

As a second reagent solution, there was used a 50 mM MOPS-NaOH buffer solution (pH 7.4) containing 2.0 mg Ab/ml anti-human CRP goat serum (available from Wako Pure Chemical Industries, Ltd.), 150 mM NaCl and 0.1 w/v % $NaN_3$.

(4) CRP Value Measurement by Immunoturbidimetry

Measuring Procedure

The CRP concentration of each sample for measurement was determined by the same procedure as described in Example 1, (4).

Results

The results obtained are shown in Table 2.

TABLE 2

| | Investigation on Magnesium Ion Concentration | | | | | | |
|---|---|---|---|---|---|---|---|
| RF in sample for measurement (IU/ml) | Magnesium chloride concentration at reaction | | | | | | |
| | CRP value (mg/dl) | | | | | | |
| | 0 mM | 10 mM | 30 mM | 50 mM | 100 mM | 150 mM | 300 mM |
| 18 ↓ | 0.22 | 0.21 | 0.21 | 0.23 | 0.22 | 0.24 | 0.22 |
| 205 | 0.59 | 0.55 | 0.41 | 0.30 | 0.31 | 0.29 | 0.27 |
| 410 | 0.85 | 0.82 | 0.50 | 0.32 | 0.29 | 0.27 | 0.28 |

From the results shown in Table 2, it can be seen that measurement errors due to RF can be markedly reduced by the presence of 30 to 300 mM of magnesium ions at the time of the reaction.

Although not shown in Table 2, the following result was obtained: when the same measurement as above was carried out except for changing the magnesium ion concentration to 350 mM, the CRP value was decreased even in the case of a sample for measurement having a RF value of zero. This fact indicates that when the magnesium ion concentration is too high, the antigen-antibody reaction is depressed (inhibited).

EXAMPLE 3

Reduction of the influence of Clq on the measurement (1) Samples for Measurement Samples for measurement were prepared by adding purified human Clq (available from Sigma Chemical Co.) to each of two human serum samples (RF: 23 IU/ml and 27 IU/ml, respectively) to adjust the Clq concentration to a predetermined concentration. The RF values were measured by use of RF-HA Test Wako (mfd. by Wako Pure Chemical Industries, Ltd.) according to the standard procedure described in the operating manual.

(2) Samples for Obtaining a Calibration Curve

Physiological saline (150 mM NaCl; CRP concentration: 0 mg/dl) and CRP standard (available from Wako Pure Chemical Industries, Ltd.; CRP nominal value: 6.2 mg/dl) were used as samples for obtaining a calibration curve.

(3) Reagent Solutions for Reaction

① Buffer Solutions (First Reagent Solutions)

As first reagent solutions, there were used 50 mM MOPS-NaOH buffer solutions (pH 7.4) containing 3.0 w/v % polyethylene glycol 6,000, 0.1 w/v % $NaN_3$ and 150 mM sodium chloride (or magnesium chloride).

② Anti-CRP Solution (Second Reagent Solution)

As a second reagent solution, there was used a 50 mM MOPS-NaOH buffer solution (pH 7.4) containing 1.0 mg Ab/ml anti-human CRP goat serum (available from Wako Pure Chemical Industries, Ltd.), 150 mM NaCl and 0.1 w/v % $NaN_3$.

(4) CRP Value Measurement by Immunoturbidimetry

Measuring Procedure

The CRP concentration of each sample for measurement was determined by the same procedure as described in Example 1, (4).

Results

The results obtained are shown in Table 3.

TABLE 3

| | Reduction of Influence of Clq on Measurement | | | |
|---|---|---|---|---|
| Clq in sample for | 150 mM sodium chloride | | 150 mM magnesium chloride | |
| measurement (mg/dl) | Serum A CRP value | Serum B (mg/dl) | Serum A CRP value | Serum B (mg/dl) |
| 0 | 0.31 | 1.76 | 0.31 | 1.68 |
| 16 | 0.33 | 1.99 | 0.32 | 1.59 |
| 32 | 0.41 | 2.04 | 0.29 | 1.61 |
| 63 | 0.48 | 2.11 | 0.29 | 1.61 |
| 125 | 0.55 | 2.26 | 0.31 | 1.65 |
| 250 | 0.62 | 2.46 | 0.31 | 1.68 |
| 500 | 0.74 | 2.77 | 0.31 | 1.72 |

From the results shown in Table 3, it can be seen that measurement errors due to Clq can be reduced by the presence of magnesium ions at the time of the reaction and that sodium ions do not have such an effect.

EXAMPLE 4

Reduction of influences on the measurement in heat-inactivated samples (1) Samples for Measurement As samples for measurement, there were used 73 samples in three groups, i.e., group A: 38 CRP-negative and RF-negative human serum samples, group B: 19 CRP-positive and RF-negative human serum samples, and group C: 16 CRP-positive and RF-positive human serum samples; and samples (heat-inactivated samples) prepared by placing a portion of each of the above-mentioned samples in a test tube, followed by incubation at 56° C. for 30 minutes. The RF values were measured by use of RF-HA Test Wako (mfd. by Wako Pure Chemical Industries, Ltd.) according to the standard procedure described in the operating manual.

(2) Samples for Obtaining a Calibration Curve

Physiological saline (150 mM NaCl; CRP concentration: 0 mg/dl) and CRP standard (available from Wako Pure Chemical Industries, Ltd.; CRP nominal value: 6.2 mg/dl) were used as samples for obtaining a calibration curve.

(3) Reagent Solutions for Reaction

① Buffer Solutions (First Reagent Solutions)

As first reagent solutions, there were used 50 mM MOPS-NaOH buffer solutions (pH 7.4) containing 2.0 w/v % polyethylene glycol 6,000, 0.1 w/v % $NaN_3$ and 150 mM sodium chloride (or magnesium chloride).

② Anti-CRP Solution (Second Reagent Solution)

As a second reagent solution, there was used a 50 mM MOPS-NaOH buffer solution (pH 7.4) containing 1.0 mg Ab/ml anti-human CRP goat serum (available from Wako Pure Chemical Industries, Ltd.), 150 mM NaCl and 0.1 w/v % $NaN_3$.

(4) CRP Value Measurement by Immunoturbidimetry

Measuring Procedure

The CRP concentration of each sample for measurement was determined by the same procedure as described in Example 1, (4).

Results

The results obtained are shown in Table 4.

TABLE 4

Reduction of Influences on Measurement in Heat-Inactivated Samples

| | 150 mM sodium chloride | | 150 mM magnesium chloride | |
| --- | --- | --- | --- | --- |
| | Untreated | After decomplementation | Untreated | After decomplementation |
| Group A: CRP-negative serum (CRP: less than 1.0 mg/dl) RF-negative serum (RF: not more than 30 IU/ml) | | | | |
| Number of samples N | 38 | 38 | 38 | 38 |
| Average mg/dl | 0.28 | 0.18 | 0.28 | 0.28 |
| Remaining rate % | — | 64.3 | — | 100.0 |
| Group B: CRP-positive serum (CRP: not less than 1.0 mg/dl) RF-negative serum (RF: not more than 30 IU/ml) | | | | |
| Number of samples N | 19 | 19 | 19 | 19 |
| Average mg/dl | 2.63 | 2.40 | 2.60 | 2.67 |
| Remaining rate % | — | 91.3 | — | 102.7 |
| Group C: CRP-positive serum (CRP: not less than 1.0 mg/dl) RF-positive serum (RF: not less than 250 IU/ml) | | | | |
| Number of samples N | 16 | 16 | 16 | 16 |
| Average mg/dl | 4.15 | 3.87 | 4.22 | 4.19 |
| Remaining rate % | — | 93.3 | — | 99.3 |

From the results shown in Table 4, it can be seen that measurement errors caused by the decomplementation can be reduced by the presence of magnesium ions at the time of the reaction. In addition, from the results obtained from the group C in Table 4, it can be seen that not only measurement errors caused by the decomplementation but also measurement errors due to RF can be reduced by the presence of magnesium ions at the time of the reaction.

As described above, the present invention provides an immunoassay method which permits suppression or reduction of measurement errors due to, for example, Clq, RF or a heat-denatured protein produced by decomplementation by heating. The present invention is effective in that application thereof makes it possible to measure an analyte to be measured, rapidly and easily with high precision and reproducibility. Therefore, the present invention contributes greatly to the art.

What is claimed is:

1. A homogeneous liquid phase immunoassay method for measuring the concentration of an analyte in a body fluid, which comprises:

treating the body fluid prior to an antigen antibody reaction by adding magnesium ions to provide a concentration of 5 to 300 mM at the time said antigen antibody reaction occurs, said magnesium ions being added:
a) to a body fluid containing the analyte to be measured, followed by mixing with a buffer solution containing an antigen or antibody to the analyte to be measured, or
b) to the buffer solution, followed by mixing with the body fluid, or
c) to both the body fluid and the buffer solution followed by mixing, the buffer serving to adjust the pH of the resulting solution, keeping the resulting solution standing for a period of time sufficient to allow said antigen-antibody reaction to take place in the presence of magnesium ions at a concentration of 5 to 300 mM previously added, and measuring a change in turbidity specific to the analyte or change in scattering light intensity specific to the analyte, which is caused by the above antigen-antibody reaction, the magnesium ions present during the measurement serving to suppress non-specific turbidity.

2. A method according to claim 1, wherein the magnesium ions are those derived from a magnesium salt.

3. A method according to claim 1, wherein the concentration of the magnesium ions in a reaction solution in which the antigen-antibody reaction is carried out is 30 to 300 mM.

4. A method according to claim 1, wherein the concentration of the magnesium ions in a reaction solution in which the antigen-antibody reaction is carried out is 50 to 300 mM.

5. An immunoassay method according to claim 1, wherein the analyte in the body fluid is C-reactive protein.

6. An immunoassay method according to claim 1, wherein the analyte in the body fluid is Antistreptolysin O.

7. A method according to claim 1, wherein the analyte to be measured is C-reactive protein, immunoglobulin G., immunoglobulin A, immunoglobulin M, Antistreptolysin O, albumin, urinary trace albumin, complement C3, complement C4, transferrin, haptoglobin, or a-fetoprotein.

8. A homogeneous liquid phase immunoassay method for determining the concentration of an analyte in a body fluid, which comprises:

treating the body fluid prior to an antigen antibody reaction by adding magnesium ions to provide a concentration of 5 to 300 mM at the time said antigen antibody reaction occurs, said magnesium ions being added:
 a) to a body fluid containing the analyte to be measured, followed by mixing with a buffer solution containing an antigen or antibody to the analyte to be measured, or
 b) to the buffer solution, followed by mixing with the body fluid, or
 c) to both the body fluid and the buffer solution, followed by mixing, the buffer serving to adjust the pH of the resulting solution, keeping the resulting solution standing for a period of time sufficient to allow said antigen antibody reaction to take place in the presence of magnesium ions at a concentration of 5 to 300 mM previously added, and measuring a change in turbidity specific to the analyte or change in scattering light intensity specific to the analyte, which is caused by the above antigen-antibody reaction, the magnesium ions present during the measurement serving to suppress non-specific turbidity, wherein said magnesium ions have a concentration of 5 to 300 mM in a reaction solution in which the antigen-antibody reaction is carried out.

9. The method according to claim 1 wherein the reaction reagent further comprises a reaction accelerator.

10. The method according to claim 8 wherein the reaction reagent further comprises a reaction accelerator.

11. A homogeneous liquid phase immunoassay method for measuring the concentration of an analyte component in a body fluid, which comprises:

treating the body fluid prior to an antigen antibody reaction by adding magnesium ions to provide a concentration of 5 to 300 mM at the time said antigen antibody reaction occurs, said magnesium ions being added:
 a) to a body fluid containing the analyte to be measured, followed by mixing a buffer solution of antigen or antibody against the analyte, or
 b) to the buffer solution followed by mixing with the body fluid, or
 c) to both the body fluid and the buffer solution, followed by mixing, the buffer serving to adjust the pH of the resulting solution, keeping the resulting solution standing for a period of time sufficient to allow said antigen antibody reaction to take place in the presence of magnesium ions at a concentration of 5 to 300 mM previously added, and measuring a change in turbidity specific to the analyte or change in scattering light intensity specific to the analyte, which is caused by the above antigen-antibody reaction, the magnesium ions present during the measurement serving to suppress non-specific turbidity caused by the presence of rheumatoid factor or other substances causing non-specific turbidity.

12. A homogeneous liquid phase immunoassay method for measuring the concentration of an analyte component in a body fluid selected from the group consisting of C-reactive protein immunoglobulin G, immunoglobulin A, immunoglobulin M, Antistreptolysin O, albumin, complement C3, complement C4, transferrin, haptoglobin and afetoprotein, which comprises:

treating the body fluid prior to an antigen antibody reaction by adding magnesium ions to provide a concentration of 5 to 300 mM at the time said antigen antibody reaction occurs, said magnesium ions being added:
 a) to a body fluid containing the analyte to be measured, followed by a mixing buffer solution of antigen or antibody against the analyte, or
 b) to the buffer solution, followed by mixing with the body fluid, or
 c) to both the body fluid and the buffer solution, followed by mixing, the buffer serving to adjust the pH of the resulting solution, keeping the resulting solution standing for a period of time sufficient to allow said antigen-antibody reaction to take place in the presence of magnesium ions at a concentration of 5 to 300 mM previously added, and measuring a change in turbidity specific to the analyte or change in scattering light intensity specific to the analyte, which is caused by the above antigen-antibody reaction, the magnesium ions present during the measurement serving to suppress non-specific turbidity caused by the presence of rheumatoid factor or other substances causing non-specific turbidity.

* * * * *